United States Patent
Lelong

(10) Patent No.: US 6,190,320 B1
(45) Date of Patent: Feb. 20, 2001

(54) METHOD FOR THE PROCESSING OF MEDICAL ULTRASOUND IMAGES OF BONY STRUCTURES, AND METHOD AND DEVICE FOR COMPUTER-ASSISTED SURGERY

(75) Inventor: Pierre Lelong, Nogent-sur-Marne (FR)

(73) Assignee: U.S. Philips Corporation, New York, NY (US)

(*) Notice: Under 35 U.S.C. 154(b), the term of this patent shall be extended for 0 days.

(21) Appl. No.: 09/407,777

(22) Filed: Sep. 28, 1999

(30) Foreign Application Priority Data

Sep. 29, 1998 (FR) .................................... 98 12160

(51) Int. Cl.$^7$ ....................................................... A61B 8/00
(52) U.S. Cl. ............................................. 600/439; 600/443
(58) Field of Search .................................... 600/443, 442, 600/444, 437, 438, 439

(56) References Cited

U.S. PATENT DOCUMENTS

| 5,268,967 | * | 12/1993 | Jang et al. | 382/6 |
| 5,457,754 | | 10/1995 | Han et al. | 382/128 |
| 6,010,646 | * | 8/2000 | Napolotano et al. | 600/443 |

FOREIGN PATENT DOCUMENTS

| 4135881 | 5/1993 | (DE) | G06F/15/70 |
| 0840252 | 3/1998 | (EP) | G06T/5/00 |

OTHER PUBLICATIONS

"Computer–Assisted Spinal Surgery Using Anatomy–Based Registration" by Stephane Lavallee, Philipsse Cinquin et al., published in "Computer–Assisted Spine Surgery", Article No. 32, pp. 425–448.

* cited by examiner

Primary Examiner—Marvin M. Lateef
Assistant Examiner—Maulin Patel
(74) Attorney, Agent, or Firm—John F. Vodopia

(57) ABSTRACT

The image processing method according to the invention includes a step for the acquisition, by means of an ultrasound transducer, of a digitized echographic image of a structure which is substantially not transparent to the ultrasound waves, and a step for the extraction of contour points of said structure. In order to automate the extraction of points, the method includes sub-steps for the detection, in the columns of points of the digitized echographic image, of points which locally have a maximum intensity along each column, for the chaining of points detected from one column to another in a predetermined vicinity, and for selecting chains in the digitized echographic image by determining the chain nearest to the ultrasound transducer as being the contour of said structure. The device according to the invention carries out a method for the simultaneous representation, during the operation, of a high-resolution pre-surgery image and virtual operating tools which are superinposed in this image, together with their current location and orientation as determined in a marking system as a result of the processing of the echographic image.

8 Claims, 5 Drawing Sheets

METHOD FOR THE PROCESSING OF MEDICAL ULTRASOUND IMAGES OF BONY STRUCTURES, AND METHOD AND DEVICE FOR COMPUTER-ASSISTED SURGERY

BACKGROUND OF THE INVENTION

1. Field of the Invention

The invention related to a method for the processing of medical ultrasound images of bony structures. The invention also relates to a method and a device for computer-assisted surgery utilizing said method. The invention is used in the field of apparatus for computer-assisted surgery which include a medical image acquisition system, a work station and an image display system.

2. Description of Related Art

One field of application is that of spinal or orthopedic surgery or, generally speaking, surgery performed on a bony structure. In these cases the surgical intervention may include the insertion of a linear tool, such as a screw or a pin, into the bony structure. For example, in the case of spinal surgery, being the most difficult, a first problem exists in that the operation must be carried out without damaging the nerves, the spinal cord and the vessels. Screws are generally inserted into a vertebral pedicle at a specific angle and are buried at this angle in order to be inserted into the vertebral body as far as exactly the axis of the pedicle. This operation requires a very exact localization of the axis of the pedicle. In the case of surgery without assistance from an imaging system, it is estimated that 30% of the pedicular screws are incorrectly positioned in the case of lumbar vertebrae and that until this day surgery on dorsal and cervical vertebrae is impossible for reasons of lack of precision, because these vertebrae are much smaller than the lumbar vertebrae. A second problem consists in carrying out this type of operation with precision even in the case of severe deformation of the bony structures, so a situation far from statistically deduced a priori knowledge of the shape of the bony structures involved, that is to say far from the known standard model. A third problem consists in that the bony structures do not lend themselves for the formation of images with given types of waves. It is possible to form pre-surgery X-ray images therefrom which are convenient and very exact without excessively exposing the patient, but it is difficult, if not impossible, to operate in the presence of X-rays considering the risk of excessive exposure of the patient as well as the surgeon. However, generally ultrasound is not used in conjunction with bony structures because it is known that the ultrasound waves do not penetrate bony structures and that these waves even have difficulty in traversing the ligaments which join the bones at the area of articulations. At present it is difficult to visualize an articulation, or vertebrae, by means of ultrasound images without removing the ligaments in question from the trajectory of the ultrasound beam; on the other hand, the ultrasound waves are hazardous neither to the patient nor to the surgeon and, therefore, ultrasound images may be formed during an operation.

From the article "Computer-Assisted Spinal Surgery Using Anatomy-Based Registration" by Stéphane LAVALLEE, Philippe CINQUIN. et al., published in "Computer-Assisted Spine Surgery", Article No. 32, pp. 425–448, it is already known to use a pre-surgery image, acquired by digital tomography (being an X-ray imaging technique), in co-operation with a so-called "ultrasound pointer" reference system (FIG. 32-12 of the cited publication). The object is to match an ultrasound image formed in the course of the surgical intervention with the pre-surgery X-ray image so that the surgeon can carry out, in a marked zone in the ultrasound image, a surgery plan which is defined in the X-ray image and includes the positioning of tools in an appropriate location and with an appropriate orientation. In order to achieve matching of the X-ray image and the ultrasound image, diode devices are fixed on the one hand to a bony structure of the patient in order to form a reference and to a transducer of an ultrasound echograph on the other hand, thus forming a marking system. A matching algorithm is then used to make the bony structure, represented in the pre-surgery X-ray image, register with points situated on the wave front reflected by the same bony structure which is reproduced in the ultrasound image acquired during the operation.

The method which is known from the cited publication enables the acquisition of small segments of plane curves in the ultrasound image on the basis of the fact that the upper part of the thick edges represented in the ultrasound image constitutes the true edge of the bony structure because it corresponds to the front of the wave reflected by this bony edge, which arrives first from the transducer which is positioned in the upper part of the image. The known method has been tested only on samples of vertebrae outside the body of a patient. In the hypothetical case of an application for a real operation on a patient, a difficulty is encountered in that the known method is not automated. It is actually difficult to control such a delicate operation while utilizing a method which is not automatic and is not carried out in real time. The cited publication does not provide any indication which could lead to means for automation. Citation of a reference herein, or throughout this specification, is not to construed as an admission that such reference is prior art to the Applicant's invention of the invention subsequently claimed.

SUMMARY OF THE INVENTION

It is an object of the present invention to provide a method for the processing of an ultrasound image of a structure which is not very transparent to ultrasound, such as a bony structure, which method includes steps for the automatic extraction of contour points of said structure, said steps being carried out in real time.

The objects according to the invention are achieved by means of an ultrasound image processing method including a step for the acquisition, utilizing an ultrasound transducer which is coupled to an echographic device, of a digitized echographic image of a structure which is substantially not transparent to the ultrasound waves, and a step for the extraction of contour points of said structure, the step for the extraction of points being automated by way of the following sub-steps: detection, in columns of points of the digitized echographic image, of points of a locally maximum intensity along each column, chaining of the detected points from one column to another in a predetermined neighborhood, selection of chains in the standard echographic image by determining the chain nearest to the ultrasound transducer as being the contour of said structure.

The method according to the invention offers several advantages. It provides a more exact contour in an ultrasound image than the known method, and also a contour which is substantially longer in relation to the ultrasound image field, thus enabling better matching of the pre-surgery image and the ultrasound image. Moreover, because this method can be carried out automatically and in real time on the basis of the image data derived in situ, the position of this exact contour can be updated during the surgical operation, so that the matching of the ultrasound image and the pre-surgery image can be suitably updated.

For one application a computer-assisted surgery method is proposed for a surgical operation in the field of bone surgery.

A problem linked to such a method resides in the fact that the step for the acquisition of ultrasound images yields information relating to the front wave reflected by the bony structure, which information is not very exact, or even non-existent, because a variety of other, non-bony structures which, however, are also non-transparent to ultrasound, mask the bony structure and disturb or even prevent the reflection of the ultrasound waves. Therefore, in such a case the step for matching the ultrasound image and the pre-surgery image may also be less exact. This problem is solved according to the invention by means of the surgery method including acquisition of a pre-surgery image, having a substantially high resolution, of a zone of a bony structure selected for a surgical operation, segmentation of the pre-surgery image in order to determine a contour of the bony structure, acquisition, during an operation, of at least one digitized echographic image of a zone of the same bony structure, said image being associated with measurements of the location and orientation in a marking system with fixed marking, automatic extraction of contour points, in conformity with the methods of this invention, of the digitized echographic image in order to supply contour points of the bony structure in real time during the operation, together with their location and orientation in the marking system;

matching the contour of the bony structure of the segmented pre-surgery image with contour points extracted from the echographic image in order to locate and orient the pre-surgery image in the marking system, simultaneous representation of the pre-surgery image, marked in the marking system, and surgical tools in the form of virtual images superposed on said image, representing real surgical tools used during the operation, together with their current location and orientation determined in the marking system.

For another application there is proposed a computer-assisted surgery device which includes means for carrying out such a method in the field of bone surgery.

BRIEF DESCRIPTION OF THE DRAWING

The invention will be described in detail hereinafter with reference to the accompanying diagrammatic drawings; therein.

DETAILED DESCRIPTION OF THE PREFERRED EMBODIMENT

The invention relates to a process for the processing of ultrasound images. The invention also relates to a method for assisted surgery which includes steps of such a process. The invention, moreover, relates to a device for computer-assisted surgery which is intended for use in the field of bone surgery and includes means for carrying out said method.

Figure 5:
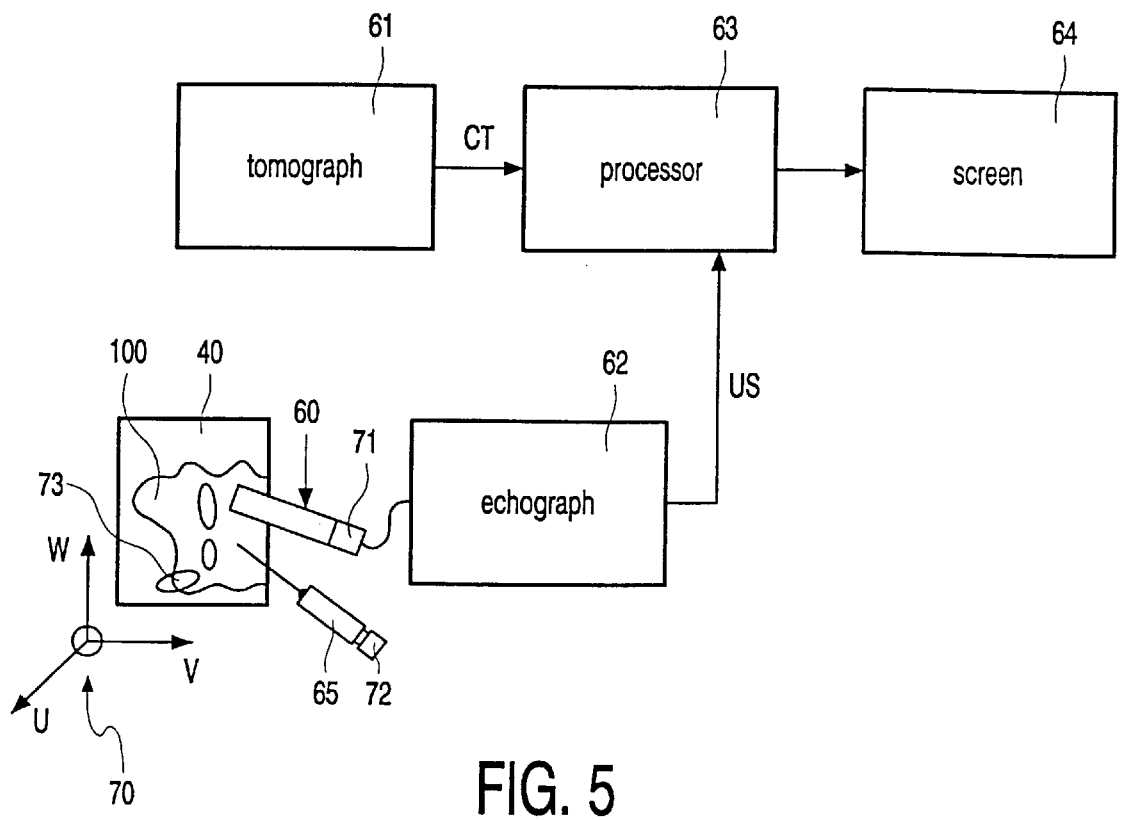
FIG. 5 illustrates a device for computer-assisted surgery.

As is illustrated by the functional blocks in FIG. 5, the device for computer-assisted surgery includes means for providing an exact location and orientation of surgical tools 65, used during a surgical operation, with respect to a bony structure 100 which is situated in an operative field 40, and for visualizing said surgical tools with their exact location and orientation in a three-dimensional high-definition image corresponding to the operating field. The device notably includes means for the acquisition of medical image data which are connected to a processor which executes the steps of method for assisted surgery and a system for the display of medical images which is connected to the processor. The image data acquisition means include at least means 61 for the acquisition of a high-definition pre-surgery image CT of a bony structure to be operated, and means 60, 62 for the acquisition of an intra-surgical ultrasound image US of a zone of the same bony structure 100 to be operated. The acquisition of the high definition three-dimensional pre-surgery image CT of the bony structure to be operated can be realized notably by means of a magnetic resonance imaging apparatus 61 or a digital tomography apparatus 61 based on X-ray images. The acquisition of the ultrasound image US can be performed by means of an ultrasound transducer which may be a standard probe 60 which is coupled to an echograph 62. The device for assisted surgery also includes display means 64, for example a screen, for the visualization of the tools in the high-definition image. This device may also include recording means. The visualization can be realized by simultaneously reproducing, during the surgical operation, the three-dimensional pre-surgery image CT and the tools 65 in the form of three-dimensional virtual objects on the screen 64. In order to realize such a simultaneous reproduction, the device includes on the one hand means 70, 71, 72, 73 for determining the exact location and the orientations in three dimensions, relative to the bony structure to be operated, of the real surgical tools 65 used and manipulated by the surgeon during the operation, and on the other hand a processor 63 for applying to the virtual tools the location and the orientations in three dimensions of the real tools and to enable the surgeon to visualize in the high-definition image the location and the orientations of these real tools, applied according to an appropriate operating plan. The means for the localization and determination of the orientations of the bony structure and the real tools during the operation consist of a marking system which includes a fixed marking device 70 in the operating room, a marking device 73 which is associated with the bony structure, a marking device 71 which is associated with the ultrasound transducer 60, and a marking device 72 which is associated with each tool 65 used. The location and the orientation of the marking devices associated with the bony structure, the transducer and the real tools are determined in relation to the fixed marking device 70. The marking devices are advantageously of the type which includes three LEDs. Such diode devices are known to those skilled in the art. The surgical tools 65 may include a drill, pins, screws etc. The microprocessor 63 constitutes an important element of the device for assisted surgery that controls and executes a method for assisted surgery for making the pre-surgery image CT register with the operating field 40.

This method for assisted surgery according to the invention includes steps for the automatic and real-time processing of the ultrasound image and will be described in detail hereinafter, by way of example, for an application involving the processing of images of the spinal column. The concept of computer-guided surgery offers the advantage that surgery performed on the spinal column is more exact and reliable. The method for assisted surgery has for its object to acquire the ultrasound image US in the marking system and to match the pre-surgery image CT with the ultrasound image US in order to make the pre-surgery image CT register with the operating field 40.

Figure 1A:
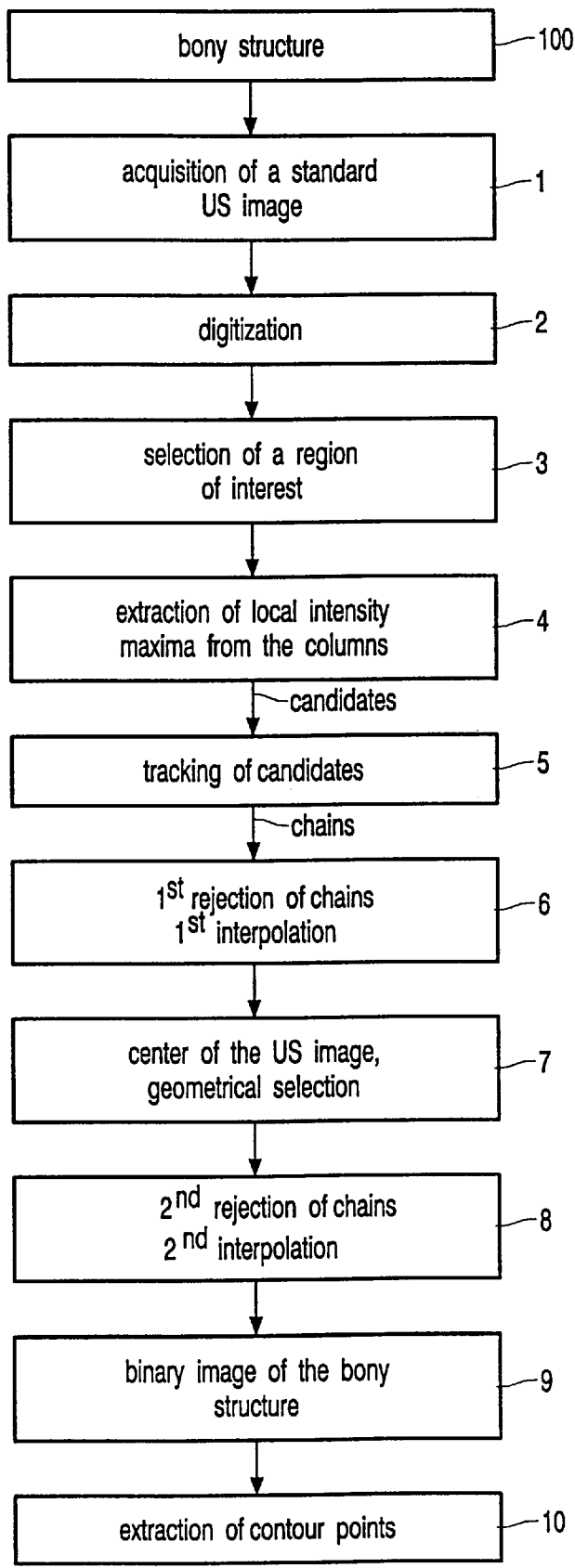
FIG. 1A shows the execution of the steps of the method for the processing of ultrasound images US in the form of a diagram with functional blocks.
Figure 1B:
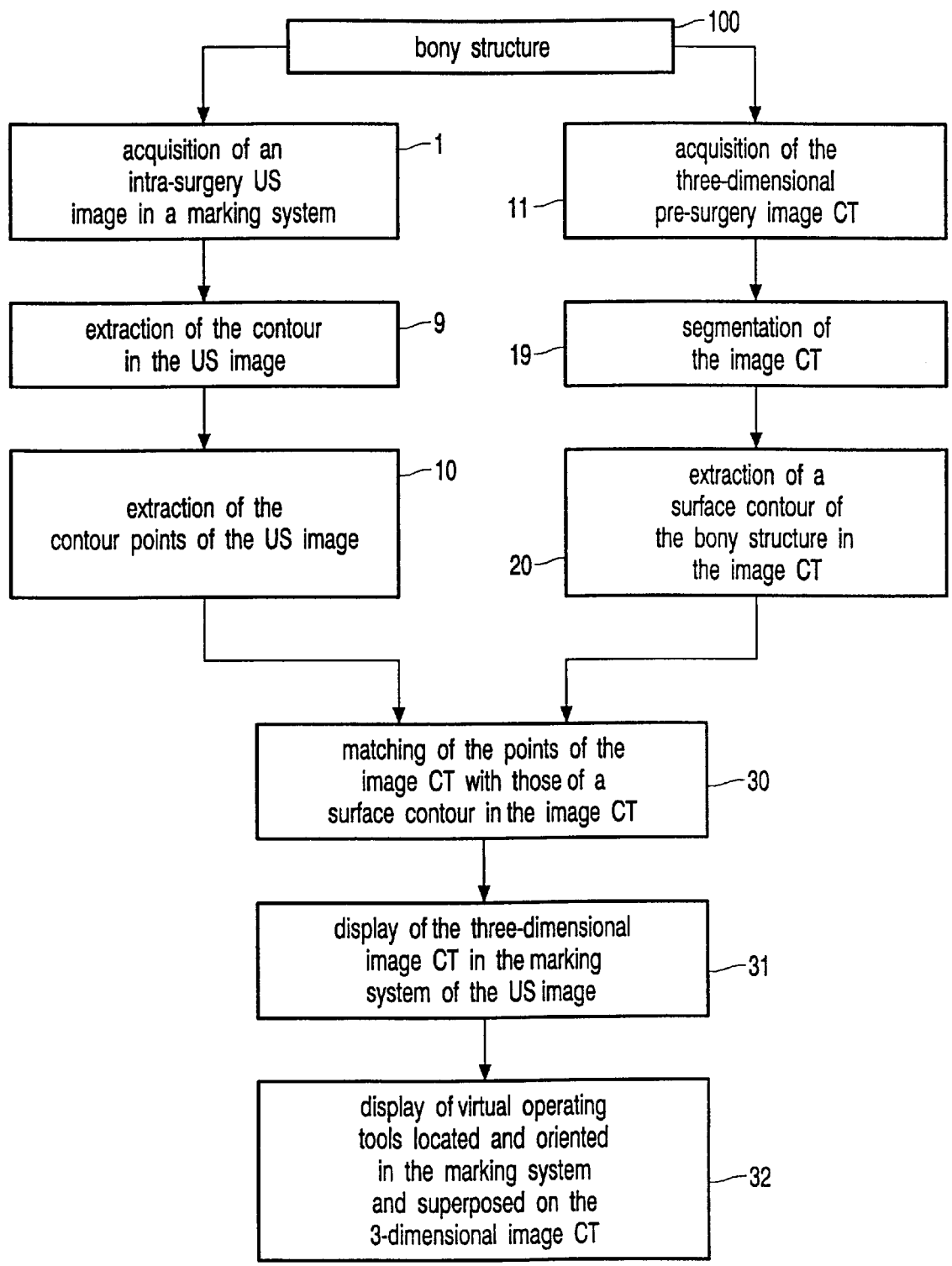
FIG. 1B shows the execution of the computer-assisted surgery method.
Figure 4A:
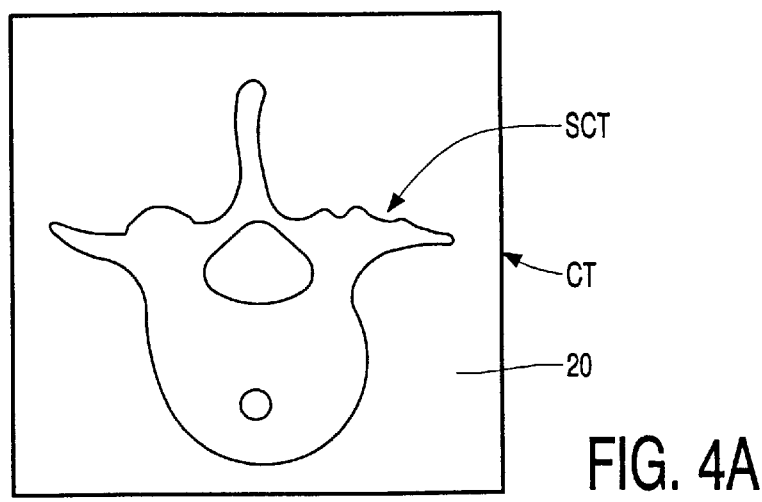
FIG. 4A shows a bony structure surface (vertebra) extracted from an image CT.

As is represented by the functional blocks of FIG. 1B, the method for assisted surgery includes the following steps:

a) Acquisition 11 of a high-definition three-dimensional pre-surgery digital image CT of the bony structure to be operated on, utilizing the image acquisition means 61.

b) Segmentation 19 of the image CT by means of known contour extraction means.

c) Extraction 20 of the surface of the bony structure in the segmented image CT. The bony structure is then represented by a binary volume of voxels having intensity values 0 or 1, depending on whether or not they belong to the surface of this structure. The extracted surface SCT is shown in FIG. 4A.

d) Carrying out an ultrasound image processing method for a zone of the same bony structure, including specifically the extraction of points of the contour of the bony structure which are localized in the reference system; this operation is illustrated by the functional blocks of FIG. 1A and includes the following steps:

1) Acquisition 1 of an ultrasound image US of a zone of the bony structure, that is to say a part of a vertebra, at the beginning of the surgical operation. To this end, the surgeon exposes the bony structure to be operated and performs, using the transducer 60 associated with the ultrasound device 62, an acquisition of at least one standard ultrasound image. Such an image acquisition is performed, for example by filling the cavity formed by the operative field with a coupling medium, for example a physiological serum, and by positioning the transducer 60 so that its end 67 is immersed in the serum and suitable coupling is achieved with the bony structure 100 exposed to the ultrasound waves. After the acquisition of the image, or a sequence of ultrasound images, the coupling medium may be removed by suction so that the surgeon can continue the surgical operation while using real tools 65. The ultrasound images obtained nowadays are two-dimensional. In order to obtain a threedimensional image it is necessary to record the geometrical position of the transducer 60 and to form a three-dimensional image by combining several two-dimensional images US while taking into account information relating to their respective positions. To this end, during the acquisition of an image US the marking system 70, 71, 73 records the position of the probe 60 in a system of orthogonal co-ordinates, its orientation in space by way of angles relative to coordinate axes while at the same time the corresponding ultrasound image is recorded by the device 62. The transducer 60 is, for example inclined through an angle of approximately 25 degrees relative to the vertebra and its end 67 which is immersed in the coupling medium is situated approximately 1 cm from the bony structure 100. The transducer performs a mechanical scan of the operative zone 40, yielding several ultrasound images US, for example one hundred images. The vertebra can be mechanically scanned on two sides. The ultrasound images are acquired in analog form and are digitized by means of appropriate means 2. An analog standard ultrasound image is usually obtained by ultrasound scanning along lines which form rays SCL originating from a point O in which there is located the ultrasound transducer which emits the ultrasound waves and receives the echoes returned by structures situated in the trajectory of said rays. These standard images are formed by points having an intensity level which is related to the echo returned by the structure located at the corresponding point on the ray SCL.

Figure 4B:
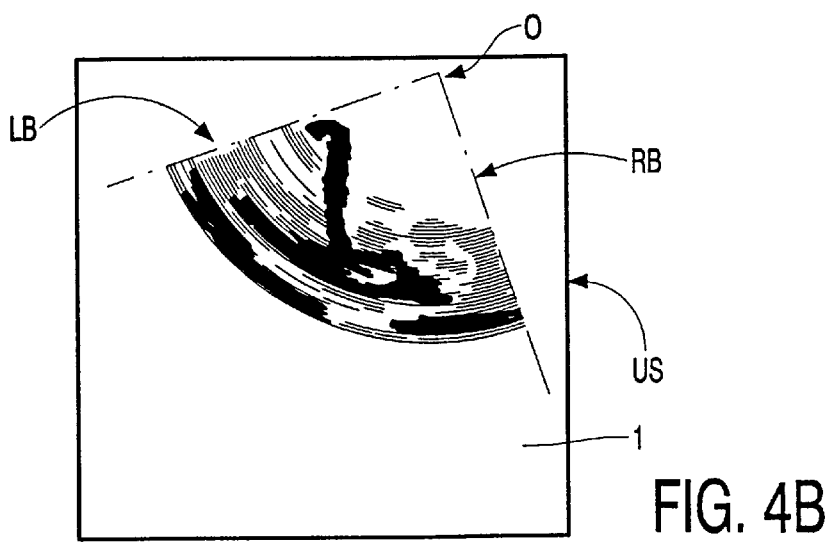
FIG. 4B shows an ultrasound image US.

2) Digitizing 2 of the standard image. A digitized ultrasound image has a rectangular shape and is formed by points of a standard image which are now marked in an orthogonal system with co-ordinates X for the columns and Y for the rows, their original intensity and original location in the standard image being maintained. The digitized ultrasound image thus obtained is shown in FIG. 4B.

It is an object of the method for assisted surgery to make contour points of the bony structure in the ultrasound image, for which it is known how to determine the position and the orientation with respect to the operative field, coincide with a corresponding contour of the bony structure in the pre-surgery image CT in order to determine the position and the orientation of this image CT in this manner. It is another object to display the image CT, which offers the advantage that it is much more exact and convenient than the ultrasound image US, on the screen 64 during the execution of the surgical operation. It is another object to superpose on said image CT virtual instruments which reproduce the shape and the motions of the real instruments 65 in real time. Therefore, it is extremely important to extract from the ultrasound image US a number of appropriate points for determining as exactly as possible the surface of the vertebra which faces the transducer.

The specific ultrasound image processing method described herein can achieve the above objects. This method offers the advantage that it yields points which define substantially long and continuous contours of the vertebra in a fully automatic fashion and in real time. As is denoted by the functional blocks of FIG. 1A, the method continues with the execution of the following steps which are carried out by means for calculation and control of the steps such as the processor 63:

3) Defining 3 a zone of interest in a region of the vertebra with surface irregularities, that is to say characteristic details, in order to supply as much useful information as possible for the respective positioning of the images CT and US. Moreover, the zone of interest is chosen so as to have a limited surface in order to include as little soft tissue as possible and also to avoid the inclusion of structures which are mobile relative to one another.

Figure 2A:
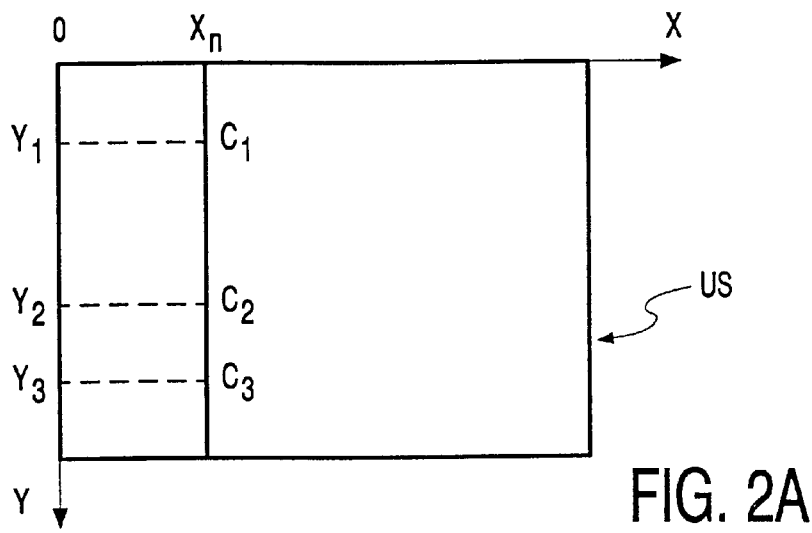
FIG. 2A illustrates the step for the extraction of local intensity maxima in a column in the digitized ultrasound image US.
Figure 2B:
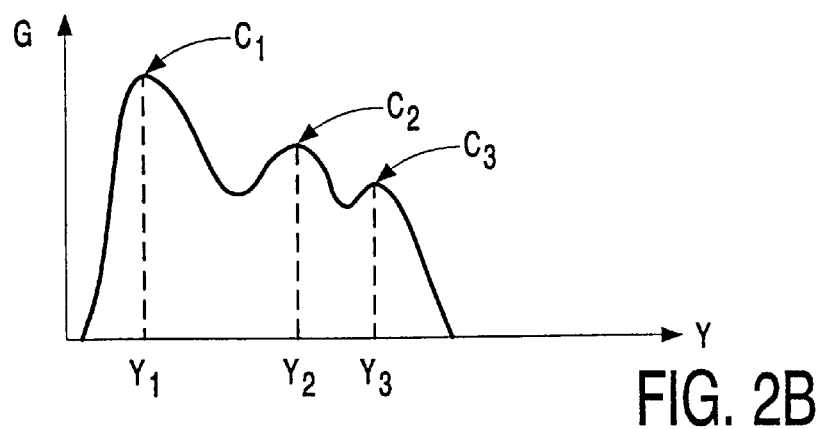
FIG. 2B shows a corresponding intensity curve G for such a column.

4) Extracting 4 so-called "best candidate" points in the digitized ultrasound image; such extraction is performed by means of the following sub-steps:

4-1) Selection of so-called "candidate" points. To this end, the digitized image US is scanned one column after the other as shown in FIG. 2A which illustrates the scanning of a column Xn in which intensity maxima C1, C2, C3 are found in the positions Y1, Y2, Y3. These "candidate" points are selected when they locally present an intensity maximum along the relevant column as illustrated by FIG. 2B which shows the values of intensity maxima G found along the column Xn in the positions Y1, Y2, Y3. In order to find consistent maxima, prior to said selection operation, there is preferably performed a low-pass filtering operation in order to diminish the noise in the digitized image US.

4-2) Intensity thresholding. A thresholding operation is performed in order to eliminate a given number of candidate points and to retain points which have an intensity level exceeding this threshold, and are called "best candidates".

5) Tracking 5 the best candidate points in the digitized image US in order to link these points and to form chains, subject to the following conditions:

Condition 1: a tracking direction is defined, for example from left to right and the best candidate points are examined.

Condition 2: any point which has not yet been admitted to a chain starts a new chain, subject to the condition that it has not been rejected previously.

Condition 3: the best candidate point, called best neighbor, is searched and selected in the successive columns which are situated nearer and nearer to the right (because of the condition 1) and at a distance which is less than a predetermined distance.

Condition 4: the best neighbors are searched and selected from left to right in neighborhoods of increasing radii, which radii however, have a predetermined maximum, said best neighbors being situated in columns.

Figure 3:
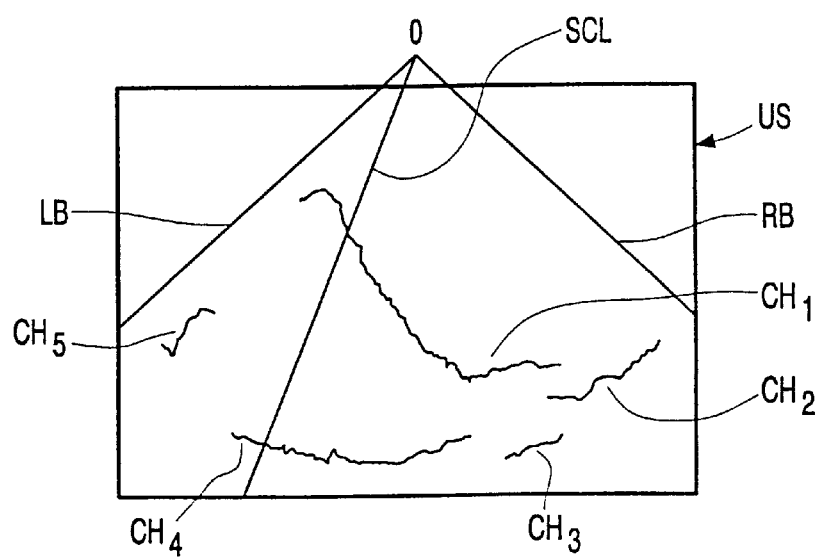
FIG. 3 illustrates the selection of chains in the digitized ultrasound image US.

Condition 5: all best candidate points which are not included in a chain are eliminated. 6) first selection 6 of chains as illustrated in FIG. 3 which shows an image US in which several chains CH1, CH2, CH3, CH4, CH5 have been determined subject to the conditions:

Condition 6: any chain having a length smaller than a reference length, measured in points, is eliminated. For example, the reference length is: 8 points.

Condition 7: when the chains include gaps of a few points (for example, 1 point), these gaps are filled by interpolation. For example, in the case where a column has no point, a localized point is attributed thereto by performing a linear interpolation between the points which satisfy the condition 3 and are situated in the column to the left and in the column to the right of the empty column.

In this context it is not relevant whether the term condition or criterion is used. 7) Geometrical selection 7 for determining the contour of bony structures and for eliminating the internal zones illustrated in FIG. 3.

7-1) Determination of the central point O of the digitized echographic image US. The echographic image US is characterized by the radial lines SCL of the ultrasound scan which emanate from the center O and correspond to the ultrasound transducer. The center O is determined with precision, on the basis of said ultrasound image US itself, at the intersection of the radial lines at the left and right edges LB and RB.

7-2) Actual geometrical selection, including an examination of the location of chains, such as CH1 to CH5, found in the digitized image US in the preceding tracking step. Each radial scan line SCL is considered as from the central point O, while proceeding away from the center O, by an oriented radial scan operation of the echographic image in which each first detected point, relating to a radial scan line as well as to a chain, is saved. This step enables determination of the echographic wave front and hence enables selection of the contour points of the bony structure in relation to points inside the bony structure or other structures. For example, in FIG. 3 the chains CH1 and CH2 will be saved.

8) Second selection 8 of chains in conformity with the already described principle, thus eliminating the chains which are too short, for example the chains having a length of less than 8 points. This selection is followed by a second interpolation: if there are still gaps in the chains, they are filled, for example in conformity with the previously described linear interpolation principle.

Figure 4C:
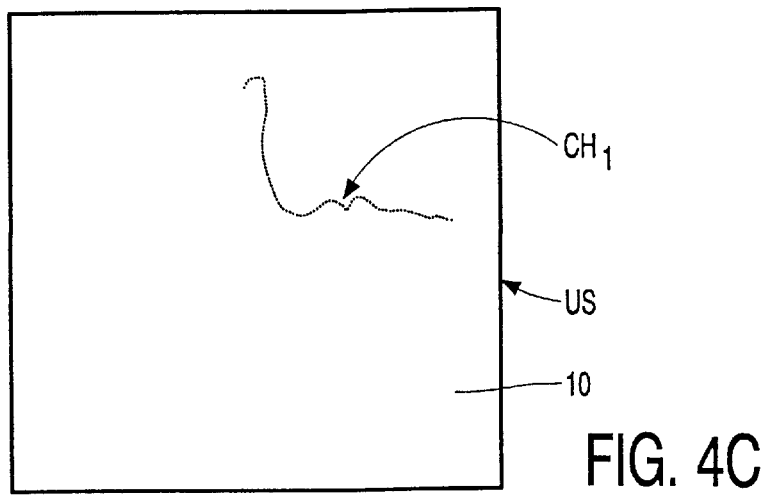
FIG. 4C shows an ultrasound image US after the extraction of contour points of the bony structure.

9) Display 9 of the image of the contours of bony structures, being a binary image containing the chains corresponding to the external contour, for example of vertebrae, that is to say the contour which faces the ultrasound transducer. For example, in FIG. 4C only the chain CH1 is saved after the selection steps.

10) Extraction 10 of contour points. These points will be used for realizing the matching with the image CT.

Figure 4D:
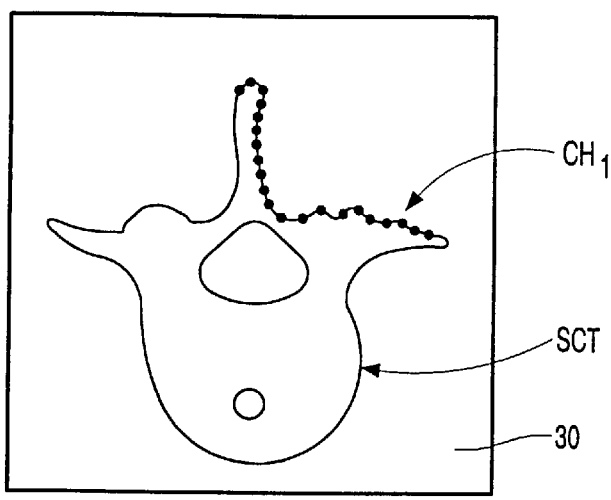
FIG. 4D shows the result of the matching of the processed images US and CT.

The method for assisted surgery will continue with the following steps:

e) Calibration of the images CT and US and adjusting them to the same scale. This step is performed by means of any known appropriate means. It is assumed that in first approximation these images are free from distortions.

f) Matching 30 the pre-surgery image CT and the image US of the contours. The matching of the image of the contours, produced by the processing of the pre-surgery image CT, with the image of the contour points, yielded by the processing of the digitized image US, is performed by means of any appropriate image matching algorithm which is known from the state of the art and converges while yielding an image of contours of the image CT and superposed contour points of the image US. The contours extracted and determined in the image US by means of the method according to the invention are substantially long and very exact. In these circumstances the convergence of the algorithm is fast and provides exact localization of bony structures in the pre-surgery image CT in three dimensions relative to the operating field in the fixed marking system. This step is illustrated in FIG. 4D which shows the matching of the chain CH1 of the image US with the extracted surface SCT of the image CT.

g) Representation 31, on a screen 64, of the high definition three-dimensional pre-surgery image CT in coincidence with the operating field, and display 32 of virtual surgical tools which represent real tools 65. The virtual tools are superposed in this image 31. The real surgical tools 65 are provided with marking devices 72 with LEDs which provide measures of their positions and their orientations in the orthogonal co-ordinate system defined above. In conformity with these measures, the virtual tools are positioned and oriented in three dimensions relative to the bony structure of the high- definition three-dimensional pre-surgery image.

Using this method for assisted surgery, because of the exact three-dimensional visualization of the virtual tools the surgeon can position the real surgical tools with the required precision relative to the real bony structure. Therefore, given surgical operations which could not be carried out thus far now become feasible.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for the processing of images comprising:

acquiring, utilizing an ultrasound transducer which is coupled to an echographic device, a digitized echographic image of a structure which is substantially not transparent to the ultrasound waves, and extracting contour points of said structure, the step of extracting contour points further comprising detecting, in columns of points of the digitized echographic image, points of a locally maximum intensity along each column, chaining of the detected points from one column to another in a predetermined neighborhood, and selecting chains in the standard echographic image by determining the chain nearest to the ultrasound transducer as being the contour of said structure.

2. A method as claimed in claim 1, in which the chaining step further comprises defining an intensity threshold for the chained points, defining a chaining direction, starting from a first column towards a last column from one edge to an opposite edge of the digitized image, and defining a neighborhood as a reference distance in a predetermined branch in order to chain two points in different columns.

3. A method as claimed in claim 2, in which the chaining step further comprises forming a beginning of a new chain by means of any point which does not satisfy the preceding neighborhood criterion, defining a minimum length of the chains for the saving of the chained points, and eliminating points not belonging to any chain.

4. A method as claimed in claim 3, in which the chaining step also further comprises interpolating in order to fill gaps in the chains which are smaller than a predetermined distance.

5. A method as claimed in claim 1 further comprising determining the location of the transducer in the digitized echographic image, showing radial ultrasound scan lines, by determining the intersection of two extreme radial lines in this image.

6. A method for computer-assisted surgery for performing a surgical operation on a bony structure comprising:

acquiring a pre-surgery image, having a substantially high resolution, of a zone of a bony structure selected for a surgical operation, segmenting the pre-surgery image in order to determine a contour of the bony structure, acquiring, during the surgical operation, at least one digitized echographic image of a zone of the same bony structure, said image being associated with measurements of the location and orientation in a marking system with fixed marking, automatically extracting contour points, by the method of claim 1, of the digitized echographic image in order to supply contour points of the bony structure in real time during the surgical operation, together with their location and orientation in a marking system;

matching the contour of the bony structure of the segmented pre-surgery image with contour points extracted from the echographic image in order to locate and orient the pre-surgery image in the marking system, and simultaneously representing the pre-surgery image, marked in the marking system, and surgical tools in the form of virtual images superposed on said image, which represent real surgical tools used during the operation, together with their current location and orientation determined in the marking system.

7. A computer-assisted surgery device for carrying out an operation on a bony structure comprising:

a system for the acquisition of image data, including a device for the acquisition of a high-resolution image and a device for the acquisition of ultrasound images, a marking system which includes a fixed marking device, a marking device for the bony structure to be operated on, a marking device for the means for the acquisition of ultrasound images, and a device for marking the surgical tools relative to the fixed marker, an image processing system which includes a processor which has access to the data of the images and is provided with means for carrying out the method claimed in claim 6, and a system for display and occasionally recording of image data acquired and processed by means of said method, which system is connected to the image processing system.

8. A computer-assisted surgery device as claimed in claim 7, wherein the system for the acquisition of image data further comprises means for the acquisition of a pre-surgery image, having a substantially high resolution, of a bony structure selected for a surgical operation, means for segmenting the pre-surgery image in order to determine a contour of the bony structure, and means for the acquisition, during an operation, of at least one digitized echographic image of a zone of the same bony structure, said image being associated with measurements of the location and orientation in the marking system with a fixed marker, and wherein the image processing system further comprises a microprocessor which has access to the image data and includes means for automatically extracting contour points, by the method of claim 1, of the digitized echographic image in order to produce contour points of the bony structure in real time during the operation, together with their location and orientation in the marking system;

means for matching of the contour of the bony structure of the segmented pre-surgery image and contour points extracted from the echographic image in order to locate and orient the pre-surgery image in the marking system, and means for supplying the display system with a simultaneous representation of the pre-surgery image, marked in the marking system, and surgical tools in the form of virtual images which are superposed on this image and represent real surgical tools used during the operation, together with their current location and orientation as determined in the marking system.

* * * * *